(12) United States Patent
Skoda

(10) Patent No.: US 12,148,516 B2
(45) Date of Patent: Nov. 19, 2024

(54) SYSTEMS AND METHODS FOR SMART MIXERS

(71) Applicant: Zorday IP, LLC, Mayfield Village, OH (US)

(72) Inventor: Brent M. Skoda, Mayfield Village, OH (US)

(73) Assignee: Zorday IP, LLC

( * ) Notice: Subject to any disclaimer, the term of this patent is extended or adjusted under 35 U.S.C. 154(b) by 69 days.

(21) Appl. No.: 17/751,612

(22) Filed: May 23, 2022

(65) Prior Publication Data

US 2023/0074392 A1 Mar. 9, 2023

Related U.S. Application Data

(63) Continuation of application No. 16/574,319, filed on Sep. 18, 2019, now abandoned, which is a
(Continued)

(51) Int. Cl.
*G16H 20/13* (2018.01)
*B01F 35/22* (2022.01)
(Continued)

(52) U.S. Cl.
CPC ......... *G16H 20/13* (2018.01); *B01F 35/2206* (2022.01); *B01F 35/80* (2022.01);
(Continued)

(58) Field of Classification Search
CPC .... G16H 20/13; G16H 40/63; B01F 35/2206; B01F 35/80; B01F 2101/08;
(Continued)

(56) References Cited

U.S. PATENT DOCUMENTS 8,061,149 B1 11/2011 Gowans et al.
8,550,069 B2 10/2013 Alelov
(Continued)

FOREIGN PATENT DOCUMENTS

CN 103960785 A 8/2014
WO WO-2012/006125 A1 1/2012

OTHER PUBLICATIONS

Final Office Action on U.S. Appl. No. 16/375,372 DTD Jul. 16, 2021.
(Continued)

*Primary Examiner* — Vishal Pancholi
(74) *Attorney, Agent, or Firm* — Foley & Lardner LLP

(57) ABSTRACT

An mixing device includes at least one mixing chamber, a memory, a processor coupled to the memory, and a set of instructions stored on the memory and configured to be executed by the processor. The processor is configured to determine a custom mixing recipe comprising a plurality of ingredient types and corresponding amounts for each of the plurality of ingredient types. The processor is further configured to insert the plurality of ingredient types into a first mixing chamber. A first amount of a first ingredient type and a second amount of a second ingredient type are inserted according to the custom mixing recipe. The processor is further configured to mix the plurality of ingredient types in the first mixing chamber. The processor is further configured to dispense a mixture of the plurality of ingredient types as at least one of a vapor, a fine powder, a mist, and a liquid.

20 Claims, 9 Drawing Sheets

Related U.S. Application Data continuation-in-part of application No. 16/386,600, filed on Apr. 17, 2019, now abandoned, and a continuation-in-part of application No. 16/375,372, filed on Apr. 4, 2019, now abandoned, said application No. 16/386,600 is a continuation of application No. 15/048,575, filed on Feb. 19, 2016, said application No. 16/375,372 is a continuation of application No. 15/047,332, filed on Feb. 18, 2016.

(60) Provisional application No. 62/118,869, filed on Feb. 20, 2015, provisional application No. 62/118,341, filed on Feb. 19, 2015.

(51) Int. Cl.
| | | |
|---|---|---|
| *B01F 35/80* | (2022.01) | |
| *G16H 40/63* | (2018.01) | |
| *H04L 67/01* | (2022.01) | |
| *H04L 67/02* | (2022.01) | |
| *H04L 67/025* | (2022.01) | |
| *H04L 67/10* | (2022.01) | |
| *H04L 67/1097* | (2022.01) | |
| *H04L 67/12* | (2022.01) | |
| *H04L 67/52* | (2022.01) | |
| *H04L 67/56* | (2022.01) | |
| *B01F 101/00* | (2022.01) | |
| *B01F 101/08* | (2022.01) | |
| *B01F 101/14* | (2022.01) | |
| *B01F 101/21* | (2022.01) | |

(52) U.S. Cl.
CPC .............. *G16H 40/63* (2018.01); *H04L 67/01* (2022.05); *H04L 67/02* (2013.01); *H04L 67/025* (2013.01); *H04L 67/10* (2013.01); *H04L 67/1097* (2013.01); *H04L 67/12* (2013.01); *H04L 67/52* (2022.05); *H04L 67/56* (2022.05); *B01F 2101/08* (2022.01); *B01F 2101/14* (2022.01); *B01F 2101/21* (2022.01); *B01F 2101/4505* (2022.01)

(58) Field of Classification Search
CPC .............. B01F 2101/14; B01F 2101/21; B01F 2101/4505; H04L 67/01; H04L 67/02; H04L 67/025; H04L 67/10; H04L 67/1097; H04L 67/12; H04L 67/56; H04L 67/04

See application file for complete search history.

(56) References Cited

U.S. PATENT DOCUMENTS

| | | | | |
|---|---|---|---|---|
| 8,577,734 | B2* | 11/2013 | Treyz | H04W 4/24 |
| | | | | 705/26.1 |
| 8,905,964 | B2 | 12/2014 | Poutiatine et al. | |
| 9,747,424 | B2 | 8/2017 | Sablinski | |
| 9,953,140 | B2 | 4/2018 | McLean et al. | |
| 2005/0072857 | A1* | 4/2005 | Golubev | B05B 17/0646 |
| | | | | 239/102.1 |
| 2013/0220315 | A1* | 8/2013 | Conley | A24F 40/44 |
| | | | | 128/202.21 |
| 2013/0340775 | A1 | 12/2013 | Juster et al. | |
| 2014/0060556 | A1 | 3/2014 | Liu | |
| 2014/0123989 | A1 | 5/2014 | Lamothe | |
| 2014/0174459 | A1 | 6/2014 | Burstyn | |
| 2014/0190496 | A1 | 7/2014 | Wensley et al. | |
| 2014/0246035 | A1 | 9/2014 | Minskoff et al. | |
| 2014/0261488 | A1 | 9/2014 | Tucker | |
| 2015/0038898 | A1 | 2/2015 | Palmer et al. | |
| 2015/0122252 | A1 | 5/2015 | Frija | |
| 2015/0142387 | A1 | 5/2015 | Alarcon et al. | |
| 2015/0174349 | A1 | 6/2015 | Tunnell et al. | |
| 2015/0181945 | A1 | 7/2015 | Tremblay | |
| 2015/0196060 | A1 | 7/2015 | Wensley et al. | |
| 2015/0223521 | A1* | 8/2015 | Menting | A24F 40/50 |
| | | | | 131/273 |
| 2015/0224268 | A1 | 8/2015 | Henry et al. | |
| 2015/0245654 | A1 | 9/2015 | Memari et al. | |
| 2015/0250961 | A1 | 9/2015 | Whitman et al. | |
| 2015/0327596 | A1 | 11/2015 | Alarcon et al. | |
| 2015/0336689 | A1 | 11/2015 | Brown et al. | |
| 2016/0050974 | A1 | 2/2016 | Galloway et al. | |
| 2016/0089508 | A1 | 3/2016 | Smith et al. | |
| 2016/0090288 | A1* | 3/2016 | Givens, Jr. | G07F 13/065 |
| | | | | 700/283 |
| 2016/0095356 | A1 | 4/2016 | Chan | |
| 2016/0106142 | A1* | 4/2016 | Contractor | A23P 20/20 |
| | | | | 99/516 |
| 2016/0166786 | A1 | 6/2016 | Kinzer | |
| 2016/0211693 | A1 | 7/2016 | Stevens et al. | |
| 2016/0286865 | A1 | 10/2016 | King et al. | |
| 2016/0331026 | A1* | 11/2016 | Cameron | A24F 40/50 |

OTHER PUBLICATIONS

Final Office Action on U.S. Appl. No. 16/568,020 DTD Nov. 15, 2021.
Final Office Action on U.S. Appl. No. 17/721,539 DTD Feb. 14, 2023.
Final Office Action on U.S. Appl. No. 18/232,999 DTD Apr. 26, 2024.
Non-Final Office Action on U.S. Appl. No. 15/047,332 DTD Oct. 5, 2018.
Non-Final Office Action on U.S. Appl. No. 15/048,575 DTD Oct. 18, 2018.
Non-Final Office Action on U.S. Appl. No. 16/375,372 DTD Feb. 11, 2022.
Non-Final Office Action on U.S. Appl. No. 16/375,372 DTD Oct. 2, 2020.
Non-Final Office Action on U.S. Appl. No. 16/386,600 DTD Oct. 18, 2021.
Non-Final Office Action on U.S. Appl. No. 16/568,001 DTD Jan. 7, 2021.
Non-Final Office Action on U.S. Appl. No. 16/568,020 DTD Feb. 2, 2021.
Non-Final Office Action on U.S. Appl. No. 17/744,336 DTD Nov. 8, 2023.
US Office Action on U.S. Appl. No. 16/568,001 DTD Aug. 25, 2021.
US Office Action on U.S. Appl. No. 16/574,319 DTD Dec. 24, 2021.
US Office Action on U.S. Appl. No. 16/574,319 DTD Apr. 27, 2021.

\* cited by examiner

SYSTEMS AND METHODS FOR SMART MIXERS

CROSS-REFERENCE TO RELATED APPLICATIONS

This application is a continuation and claims priority to and the benefit of U.S. patent application Ser. No. 16/574,319, titled "SYSTEMS AND METHODS FOR SMART MIXERS," and filed Sep. 18, 2019, which is a continuation-in-part of, and claims priority to and the benefit of U.S. patent application Ser. No. 16/386,600, titled "SYSTEMS AND METHODS FOR INTELLIGENT VAPORIZERS," and filed Apr. 17, 2019, which claims priority to and the benefit of U.S. patent application Ser. No. 15/048,575, titled "SYSTEMS AND METHODS FOR INTELLIGENT VAPORIZERS," and filed Feb. 19, 2016, which claims priority to and the benefit of U.S. Provisional Patent Application No. 62/118,869, titled "SYSTEMS AND METHODS FOR INTELLIGENT VAPORIZERS," and filed Feb. 20, 2015; this patent application is also a continuation-in-part of, and claims priority to and the benefit of U.S. patent application Ser. No. 16/375,372, titled "SYSTEMS AND METHODS FOR MEDICAL DISPENSING, MANAGEMENT AND MONITORING," and filed Apr. 4, 2019, which claims priority to and the benefit of U.S. patent application Ser. No. 15/047,332, titled "SYSTEMS AND METHODS FOR MEDICAL DISPENSING, MANAGEMENT AND MONITORING," and filed Feb. 18, 2016, which claims priority to U.S. Provisional Patent Application No. 62/118,341, titled "SYSTEMS AND METHODS FOR MEDICAL DISPENSING, MANAGEMENT AND MONITORING," and filed Feb. 19, 2015. The contents of all of which are hereby incorporated herein by reference in its entirety for all purposes.

BACKGROUND

Use of consumer products is widespread in society. Food, electronics, cosmetics, home goods, etc. are examples of consumer products. Such consumer products can be purchased by consumers at retail stores, online, or through other methods.

SUMMARY

An illustrative mixing device includes at least one mixing chamber, a memory, a processor coupled to the memory, and a set of instructions stored on the memory and configured to be executed by the processor. The processor is configured to determine a custom mixing recipe comprising a plurality of ingredient types and corresponding amounts for each of the plurality of ingredient types. The processor is further configured to insert the plurality of ingredient types into a first mixing chamber. A first amount of a first ingredient type and a second amount of a second ingredient type are inserted according to the custom mixing recipe. The processor is further configured to mix the plurality of ingredient types in the first mixing chamber. The processor is further configured to dispense a mixture of the plurality of ingredient types as at least one of a vapor, a fine powder, a mist, and a liquid.

BRIEF DESCRIPTION OF THE DRAWINGS

Illustrative embodiments will hereafter be described with reference to the accompanying drawings.

DETAILED DESCRIPTION

Figure 1:
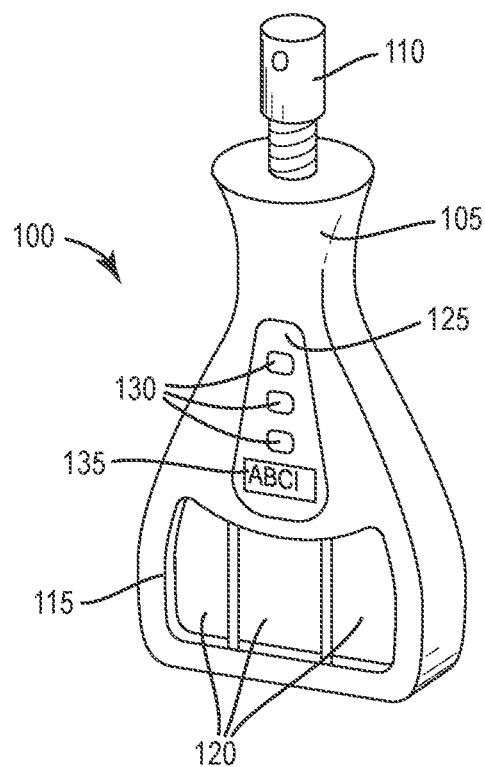
FIG. 1 is illustrates a smart mixer and dispenser in accordance with an illustrative embodiment.

Described herein are methods, systems, computer readable media, etc. for smart mixers and related technologies. In various embodiments, a smart mixer can include cartridges of various ingredients. Ingredients for a recipe, for example, may be determined based on inputs to a user interface by a user that indicate specific ingredients and specific amounts of those ingredients to be used in a mixture. In another example, a recipe may be predetermined such that the amounts and types of ingredients is known based on the predetermined recipe. The smart mixer may then insert the determined ingredients for the recipe into a mixing chamber of the smart mixer, where the ingredients are mixed together. The smart mixer may include small pumps, for example where the ingredients are liquids, that are used to insert the ingredients into the mixing chamber through tubes or other mechanisms. Once the ingredients are in the mixing chamber and mixed together, the mixture can be dispensed. Each step described above may be included in various embodiments as disclosed herein and may adjusted or duplicated in various systems and methods as disclosed herein.

The systems and methods described herein advantageously provide smart mixers for consumer products that are relatively the same size as consumer products without smart mixers that they might replace. For example, if a smart mixer is used to mix perfume, the smart mixer housing may be approximately the size of a perfume or cologne bottle. In other examples, a smart mixer may be used to mix cosmetics like makeup or shampoo, food like drinks or cereal, medicines, or other products. Each of the smart mixer housings may be approximately the same size as the packaging of those consumer products that do not have the smart mixers as disclosed herein. Accordingly, the devices, systems, and methods disclosed herein provide a way to have customizable products at their fingertips without sacrificing space other than space that would already be taken up by the packaging of those products alone.

Additionally, the systems, methods, and devices disclosed herein provide for a user to postpone specific choices regarding the products they want to consume until the last possible moment before they consume them. In this way, a user may save time and money. Buying standard consumer products at the store causes a consumer to make choices about their products (e.g., colors, types, scents, consistencies, functionalities) long before the products will be used or completely used. On the other hand, the systems and methods disclosed herein allow users to advantageously delay making such choices until right before each use of the product. Since the systems and methods herein can make custom small batches of a consumer product, the user can make specific decisions about the attributes of a product they will use each time that product is used. For example, each time a user uses perfume, they may mix a different scent of perfume using the systems disclosed herein.

The systems disclosed herein also advantageously reduce waste as a result of the features disclosed herein. For example, a user may buy makeup of a certain color. However, the user may not use all of that color of makeup before the makeup spoils and is no longer usable. In another example, the user may begin disliking the product before it is all used. Using the systems and methods disclosed herein, if a user dislikes the color of makeup, for example, the user would not mix that color of makeup again, thus never wasting resources on colors the user does not want. By postponing the choice of color for makeup, as an example, until the last possible moment before consuming, the user saves money and prevents waste.

The number of possibilities using a smart mixer in place of a typical consumer product also offers numerous choices that are not possible or at least are cost and space prohibitive. For example, using the smart devices disclosed herein, a user may use a different scent of shampoo every day for 30 days by mixing a new shampoo to use each day. By using the smart mixers as disclosed herein, the user would save significant space and money compared to buying 30 different bottles of shampoo from a retail store.

Additional waste may be reduced compared to normal consumer products using the systems and methods described herein. For example, the smart mixers and ingredient cartridges used as disclosed herein may be reused. Compared to packaging for typical consumer products, such uses would drastically decrease waste. Additionally, even if disposable ingredient cartridges were used in the systems and methods disclosed herein, the products would still create less overall waste than the standard disposable packaging of many consumer products.

FIG. 1 is illustrates a smart mixer 100 and dispenser in accordance with an illustrative embodiment. In alternative embodiments, fewer, additional, and/or different components may be included in the mixer 100. The smart mixer 100 may incorporate a computing device such as the mixer computing device 300 described below with respect to FIG. 3. The smart mixer 100 includes a housing 105 that can incorporate other various aspects of the smart mixer 100.

Included in the housing 105 is a user interface 125 and a cartridge chamber 115. The user interface 125 may be, for example, a user interface 310 of the mixer computing device 300 described below with respect to FIG. 3. The cartridge chamber 115 can house ingredient cartridges 120. The ingredient cartridges 120 are used to create a mixture in the smart mixer 100. Some or all of the ingredients from the ingredient cartridges 120 can be used for various mixtures.

The user interface 125 is an electronic display that can be interacted with by a user. The user interface 125 includes a touch screen that shows buttons 130 that can be selected by a user. Selection of any of the buttons 130 of the user interface 130 can activate software applications (apps), control functions of the smart mixer 100, control ingredients or amounts of ingredients to be used by the smart mixer 100, configure and/or start up the smart mixer 100, set up new ingredient cartridges 120, send messages and/or share recipes with other devices and/or users, and any other functions as described herein. The smart mixer 100 includes a computing device that incorporates the user interface 125. The signals received from the user interface 125 can cause the computing device to send signals to valves and pumps internal to the smart mixer 100 that control the ingredients that are inserted into a mixing chamber. Various aspects of the systems and methods disclosed herein may be powered by batteries such as rechargeable batteries. Various embodiments may also be powered by hard wired power such as through a wall outlet. The user interface 125 may also include a text input dialog 135 where alphanumeric characters may be input by a keyboard (not shown) on the user interface 125 or through voice recognition software and a microphone (not shown). In this way a user can enter text or number as desired. Such a functionality can be used in a variety of ways according to various embodiments. For example, the text input dialog 135 may be used to set ingredient amounts used in mixtures, search for other users to share recipes with, search for recipes, search for ingredients, search for software applications that can be used with the smart mixer 100, and other functionalities.

The ingredient cartridges 120, in this embodiment, are smart cartridges, in that the ingredient cartridges 120 are equipped with electronics that enable the smart mixer 100 to communicate with the ingredient cartridges 120 or identify the ingredient cartridges 120. For example, the ingredient cartridges 120 may be equipped with radio frequency identification (RFID) technology such that the smart mixer can identify types of ingredients that are in the various ingredient cartridges 120. The ingredient cartridges 120 may also have leads or connectors that connect electronically to the smart mixer 100. The ingredient cartridges 120 can then get power from the smart mixer 100 to power circuitry on the ingredient cartridges 120. For example, the ingredient cartridges 120 may include sensors to indicate how much of a particular ingredient is left in a smart cartridge. The smart mixer 100 may be connected to other computing devices as disclosed herein (e.g., through WIFi), so that the smart mixer 100 may automatically order or request the user through the user interface 125 ingredient cartridges 120 that are getting low based on the sensor signals of the ingredient cartridges 120 that the smart mixer 100 electronically communicates with. The ingredient cartridges 120 may also have a memory component that stores recipe data related to a particular ingredient in the particular cartridge. For example, if an ingredient cartridge includes a rose oil scented liquid, the memory on that ingredient cartridge may include information regarding recipes that include rose oil scents. In this way, the smart mixer 100 can read the information from the ingredient cartridge memory and determine one or more recipes that includes the ingredient stored therein.

The ingredient cartridges 120 are also interchangeable and replaceable. In other words, the smart mixer 100 is configured to be used with an unlimited number of ingredients and ingredient cartridges 120 over its lifetime. Although the ingredient cartridges 120 are smart cartridges as described above, the cartridges of various embodiments may also not be smart cartridges. In such an example, the user may input through the user interface 125 the type of cartridges that are in each slot so that the smart mixer 100 knows which ingredients are present/available for recipes. In another embodiment, the user may never input the ingredient types and the smart mixer 100 may not have information indicating the ingredients in the cartridges. In such an example, the user may, through the user interface 125, indicate specific ingredient cartridges that ingredients should be taken from and respective amounts of those ingredients for a particular recipe. In this way, the smart mixer 100 can create mixtures without knowing what ingredients are actually being used.

The smart mixer 100 also includes an internal mixing chamber (not shown). The mixing chamber is used to mix the various ingredients from the ingredient cartridges 120. In various embodiments, aspects of a mixing chamber can be controlled by the computing device in the smart mixer and the user interface 125. Mixer chambers may have different components as disclosed herein that can be used and controlled by the computing device to mix ingredients, heat/cool ingredients, pressurize/depressurize ingredients, vaporize ingredients, blend ingredients, etc. In various embodiments as described herein, a smart mixer may include more than one mixing chamber. In addition, the smart mixer 100 can include an internal dispensing chamber (not shown) from which a mixture is dispensed. A completed mixture may be inserted into the dispensing chamber from the mixing chamber. In an alternative embodiment, the mixing chamber and the dispensing chamber may be the same chamber, such that the mixture is dispensed from the same chamber it is mixed in.

In various embodiments, a smart mixer may have multiple dispensing chambers. For example, a mixing chamber may be connected to three dispensing chambers, so that a user may create and store up to three mixtures that can be dispensed at any time. In this way, a user may save their mixtures for later use, and can have multiple mixtures stored even while further mixtures are being created/mixed. In such a scenario, the user may utilize the user interface 125 to determine which of the mixtures and/or dispensing chambers should dispense a product. In the smart mixer 100, there is only a single dispenser 110, thus the user can select via the user interface 125 which mixture or which dispensing chamber should be dispensed through the dispenser 110. In alternative embodiments, the smart mixer 100 may have multiple dispensers. The multiple dispensers may each be associated with a particular dispenser chamber, such that a mixture in a particular dispenser chamber can be accessed by engaging its associated dispenser. In other embodiments, multiple dispensers may be configured to be connected to more than one dispenser chamber, such that the user can select which dispenser chamber to use to dispense a product in a particular dispenser chamber.

In FIG. 1, the smart mixer 100's dispenser 110 is a pump action spray dispenser. However, other dispensers are contemplated and disclosed herein. For example, in various embodiments, the smart mixer may in include instead of or in addition to the dispenser 110 a spigot dispenser, vaporizer dispenser, time release spray dispenser, wicking dispenser, squeeze dispenser, suction dispenser, gravity/pour dispenser, open container dispenser (such that the mixed product is accessible to the user by opening a lid or other methods, and can be accessible by a brush, scoop, hand, pouring, etc.), robotic arm/retrieval methods, and any other product dispensing methods. In some methods, an ingredient may be added as the mixture or an ingredient is dispensed. For example, in a backpack membrane water reservoir, a user may suck to drink water out of the reservoir and an ingredient may be added to the water at the suction mouthpiece. The pump action spray dispenser 110 in FIG. 1 can dispense product from a mixing chamber (or in alternative embodiments a dispensing chamber) by pressing down on the dispenser 110 to spray out a liquid or solution mixture. In an embodiment, the pump action spray dispenser 110 may also be connected to a generator, such that electrical energy can be generated from the force applied to the dispenser 110 by a user. The electrical energy can be sent to power the display of the user interface 125 and/or charge a battery that is used to power the smart mixer 100.

In an alternative embodiment, the mixing chambers of the smart mixer 100 may be omitted, such that tubes from the ingredient cartridges 120 run not to a mixing chamber, but rather to the dispenser 110. The mixing chamber can run tubes to dispenser and mix a product as it is dispensed. In such an embodiment, the computing device and the user interface 125 of the smart mixer 100 can control valves and/or pumps internal to the smart mixer 100 that control which ingredients are dispensed by the smart mixer 100. In this way, the mixture that is output at the dispenser 110 is also mixed at the dispenser or in a tube or other chamber just before the dispenser. Such an embodiment may therefore omit mixing chambers that have separate mixing steps such as blending, heating, mixing, etc.

Figure 2:
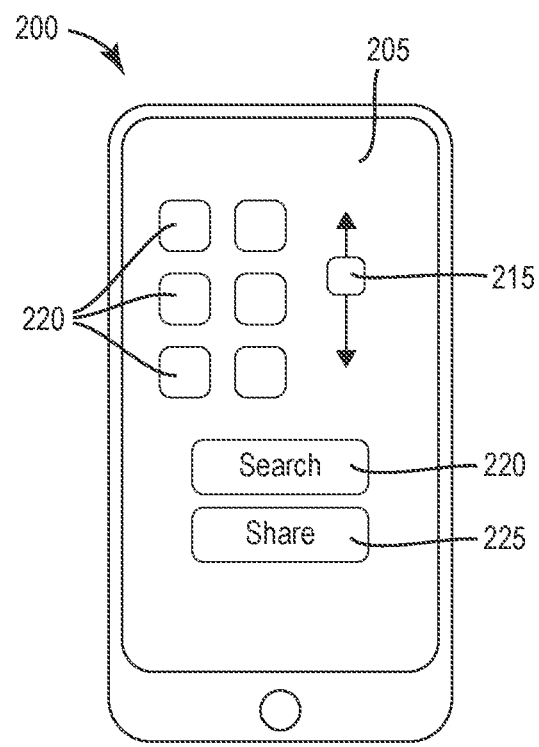
FIG. 2 illustrates a user interface for use with a smart mixer in accordance with an illustrative embodiment.

FIG. 2 illustrates a computing device 200 for use with a smart mixer in accordance with an illustrative embodiment. In alternative embodiments, fewer, additional, and/or different components may be included in the user interface. The computing device 200 shows a user interface 205 with buttons 210, slide button 215, search dialog 220, and share button 225. The computing device 200 in FIG. 2 is a mobile smart phone computing device. The user interface 205 may be displayed on a visual display such as displays of the computing device discussed below with respect to FIG. 3, such that a user can interact with the displays through the interface 360 of the computing device 350.

The computing device 200 with the user interface 205 is capable of communication with a smart mixer, such as the smart mixer 100 of FIG. 1 and described above. The communication may be through a wireless protocol, such as WiFi or Bluetooth™. The communications may allow the computing device 200 to send or receive recipes to and from a smart mixer. In this way, a user may be able to find recipes they want to create on the internet on their smart phone and send them to their smart mixer. In another example, a user may like a recipe they created using their smart mixer, so the user sends the recipe to their smart phone so it can be saved thereon and shared via the internet or other communication methods with other users.

The user interface 200 can control a smart mixer such as the smart mixer 100 of FIG. 1. For example, any of the functions described above that are implemented by a user with the user interface 125 of FIG. 1 may also be available and controlled by the user interface 205. In some embodiments, a smart mixer may not have a display or user interface such as the user interface 125 of the smart mixer 100 in FIG. 1. That is, the user interface 125 of the smart mixer 100 may be omitted in various embodiments. In such an embodiment, the user interface 205 can still be used to control the smart mixer since the controls are not available via a user interface on the smart mixer.

The user interface 205 may also provide additional functionalities. For example, the slide button 215 may be used to adjust certain ingredient amounts for a recipe by sliding the button up or down. The buttons 210 may be used to access information about recipes, access information related to ingredients available for use in the smart mixer and/or available for ordering online, access information to purchase recipes (e.g., a recipe related to a celebrity), and other information. The buttons 210 may also be used for other functionalities. For example, the buttons 210 may be used to access functionalities related to multiple smart mixers, such that the selection of a particular one of the buttons 210 causes the user interface 205 to display buttons and functionalities related to a specific smart mixer. This is valuable where, for example, a user has multiple smart mixer devices that are used for different and/or similar purposes. In various embodiments, the user interface 205 and the buttons 210 are also used to control other aspects of smart mixers as disclosed herein. For example, a dispenser of a smart mixer can be automatically controlled by the computing device 200. As just one example, a smart mixer may be controlled remotely to release a mixture through a dispenser that has been previously created. In another example, the user may set a time for when a mixture should be dispensed or mixed. In another example, the computing device 200 may be used to control a device or functionality ancillary to the smart mixer. For example, if the smart mixer mixes a batch of bread dough and dispenses it into an oven, the computing device 200 may control the functionality of the oven so that the bread can be baked at a certain time and according to certain specifications.

The user interface 205 may also be used for other functionalities such as searching, sharing, and viewing diagnostics. For example, the search dialog 220 can be used to search for recipes based on name and/or ingredient by entering text into the search dialog 220. In another example, a user may select the share button 225 to share a recipe with others via the internet, such as through an online social network or through text messaging (e.g., short message service (SMS)). In an alternative embodiment, any of the functionalities, buttons, features, dialogs, sliders, etc. discussed above with respect to FIG. 2 may be used and/or displayed on a user interface of a smart mixer, such as the user interface 125 of the smart mixer 100 described above with respect to FIG. 1.

Figure 3:
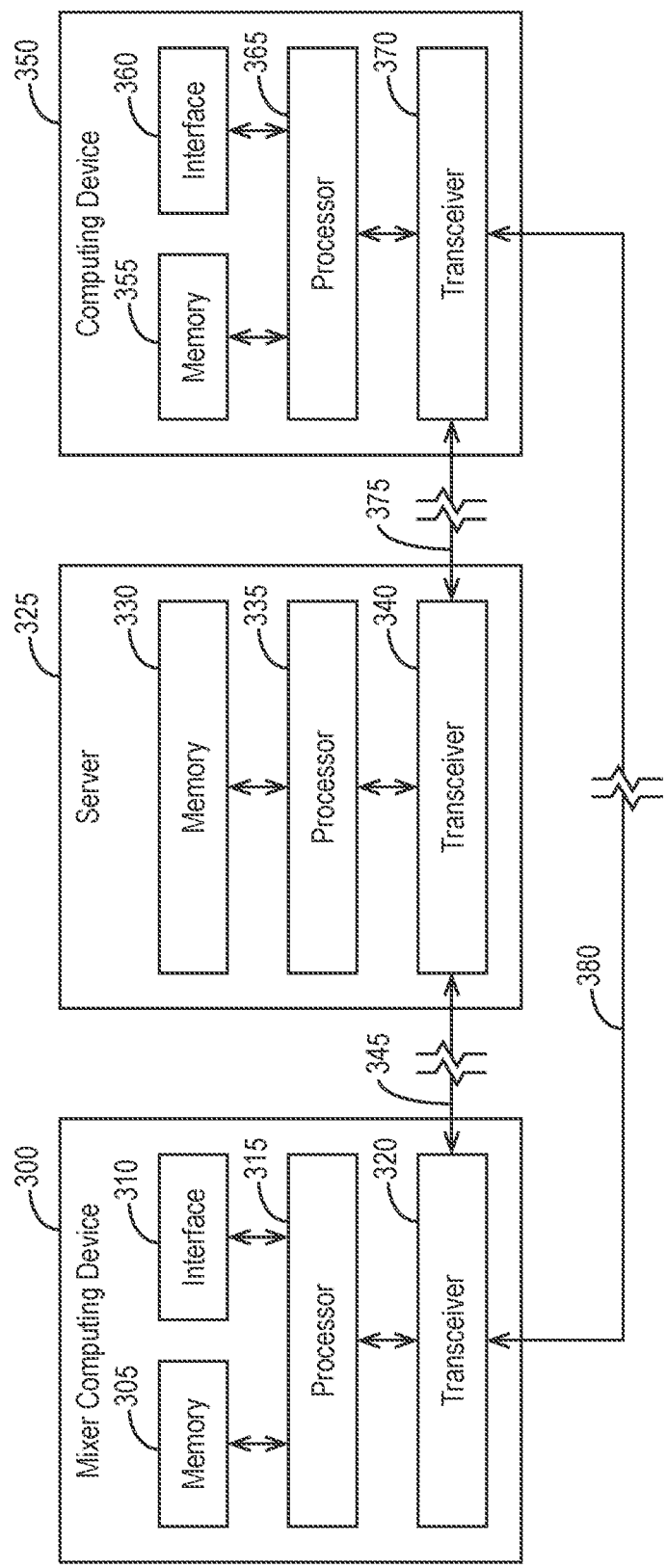
FIG. 3 is a block diagram illustrating computing devices and a server that may be used in accordance with an illustrative embodiment.

FIG. 3 is a block diagram illustrating a mixer computing device 300, a computing device 350 and a server 325 that may be used in accordance with an illustrative embodiment. In alternative embodiments, fewer, additional, and/or different components may be included in the system. The mixer computing device 300 includes a processor 315 that is coupled to a memory 305. The processor 315 can store and recall data and applications in the memory 305. The processor 315 can execute sets of instructions stored on the memory. In various examples, a set of instructions may be a mobile application (app), other software application, web browser, web application, remotely hosted application, etc. The memory 305 may store any number of software applications that can be used to effect the systems and methods disclosed herein throughout. The processor 315 may also display objects, applications, data, etc. on an interface 310. An interface may be further referred to herein as a user interface. The processor 315 is also coupled to a transceiver 320. With this configuration, the processor 315, and subsequently the computing device 300, can communicate with other devices, such as the server 325 and the computing device 350 through connections 345 and 380. The mixing computing device 300 may be used to send signals to mixing device aspects such as heaters, coolers, pumps, actuators, valves, dispensers, and any other aspects disclosed herein such that the various aspects of a smart mixer can be controlled.

The server 325 includes a processor 335 that is coupled to a memory 330. The processor 335 can store and recall data and applications in the memory 330. The processor 335 is also coupled to a transceiver 340. With this configuration, the processor 335, and subsequently the server 325, can communicate with other devices, such as the mixer computing device 300 and the computing device 350 through connections 345 and 375. The server 325 may be used to host recipes in its memory, process orders for ingredient cartridges, facilitate sharing of recipes between users, facilitate remote control of a smart mixer by providing a communication between the computing device 350 and the mixer computing device 300. The server 325 may also track usage of smart mixers. For example, signals may be sent to the server 325 through the internet every time a mixture is made or a recipe is downloaded. Therefore, such information can be tracked and aggregated across a large number of smart mixing devices 300 and computing devices 350. The server 325 may also be able to store and collect information related to ingredient cartridge usage, such as how full the cartridges are, ordering habits of consumers with respect to ingredient cartridges relative to how full a cartridge is when a new cartridge is ordered, what types of ingredients are most popular/best sellers, regional preferences of ingredients, and any other information relating to ingredients. Information may also be collected on how much certain smart mixers, certain types of smart mixers, certain ingredients, or certain recipes are used by individual consumer, by household, by region, by demographic, or by any other factor. Information may also be collected about dispensing habits such as when recipes are dispensed, how much is dispensed, how a smart mixer is controlled to dispense recipes, etc. Where data is collected by sensors, such as those described below with respect to FIGS. 6 and 7.

The computing device 350 includes a processor 365 that is coupled to a memory 355. The processor 365 can store and recall data and applications in the memory 355. The processor 365 can execute sets of instructions stored on the memory. In one example, a set of instructions may be web browser that displays and/or executes a webpage. In another example, the set of instructions is a software application stored in the memory 355 or the memory 330. The processor 365 may also display objects, applications, data, etc. on an interface 360. The processor 365 is also coupled to a transceiver 370. With this configuration, the processor 365, and subsequently the computing device 350, can communicate with other devices, such as the server 325 and the computing device 300 through the connections 375 and 380. The computing device 350 may be, for example, the computing device 200 as described above with respect to FIG. 2.

The devices shown in the illustrative embodiment may be utilized in various ways. For example, the connections 345, 375, and 380 may be varied. The connections 345, 375, and 380 may be a hard wired connection. A hard wired connection may involve connecting the devices through a USB (universal serial bus) port, serial port, parallel port, or other type of wired connection that can facilitate the transfer of data and information between a processor of a device and a second processor of a second device, such as between the mixer computing device 300 and the server 325. In another embodiment, the connections 345, 375, and 380 may be a dock where one device may plug into another device. While plugged into a dock, the client-device may also have its batteries charged or otherwise be serviced. In other embodiments, the connections 345, 375, and 380 may be a wireless connection. Such a connection may take the form of any sort of wireless connection, including but not limited to Bluetooth™ connectivity, Wi-Fi connectivity, or another wireless protocol. Other possible modes of wireless communication may include near-field communications, such as passive radio-frequency identification (RFID) and active (RFID) technologies. RFID and similar near-field communications may allow the various devices to communicate in short range when they are placed proximate to one another. In an embodiment using near field communication, two devices may have to physically (or very nearly) come into contact, and one or both of the devices may sense various data such as acceleration, position, orientation, velocity, change in velocity, IP address, and other sensor data. The system can then use the various sensor data to confirm a transmission of data over the internet between the two devices. In yet another embodiment, the devices may connect through an internet (or other network) connection. That is, the connections 345, 375, and 380 may represent several different computing devices and network components that allow the various devices to communicate through the internet, either through a hard-wired or wireless connection. The connections 345, 375, and 380 may also be a combination of several modes of connection.

To operate different embodiments of the system or programs disclosed herein, the various devices may communicate in different ways. For example, the computing device 300 may download various software applications, such as an access control app, from the server 325 through the internet. Such software applications may allow the various devices in FIG. 3 to perform some or all of the processes and functions described herein. Additionally, the embodiments disclosed herein are not limited to being performed only on the disclosed devices in FIG. 3. It will be appreciated that many various combinations of computing devices may execute the methods and systems disclosed herein. Examples of such computing devices may include desktop computers, cloud servers, smart phones, personal computers, servers, laptop computers, tablets, blackberries, RFID enabled devices, or any combinations of such devices or similar devices.

In one embodiment, a download of a program to the computing device 300 involves the processor 315 receiving data through the transceiver 320 from the transceiver 340 of the server 325. The processor 315 may store the data in the memory 305. The processor 315 can then execute the program at any time, including at a time specified by the user through the interface 310. In another embodiment, some aspects of a program may not be downloaded to the computing device 300. For example, the program may be an application that accesses additional data or resources located in the server 325. In another example, the program may be an internet-based application, where the program is executed by a web browser and stored almost exclusively in the server 325. In the latter example, only temporary files and/or a web browser may be used on the computing device 300 in order to execute a program, system, application, etc.

In yet another embodiment, once downloaded to the computing device 300, the program may operate in whole or in part without communication with the server 325. In this embodiment, the computing device 300 may access or communicate with the server 325 only when acquiring the program, system, application, etc. through the connection 345. In other embodiments, a constant or intermittent connection 345 may exist between the server 325 and the computing device 100. Where an intermittent connection exists, the computing device 300 may only need to communicate data to or receive data from the server 325 occasionally.

The configuration of the server 325 and the computing devices 300 and 350 is merely one physical system on which the disclosed embodiments may be executed. Other configurations of the devices shown may exist to practice the disclosed embodiments. Further, configurations of additional or fewer devices than the ones shown in FIG. 3 may exist to practice the disclosed embodiments. Additionally, the devices shown in FIG. 3 may be combined to allow for fewer devices or separated where more than the two devices shown exist in a system.

Figure 4:
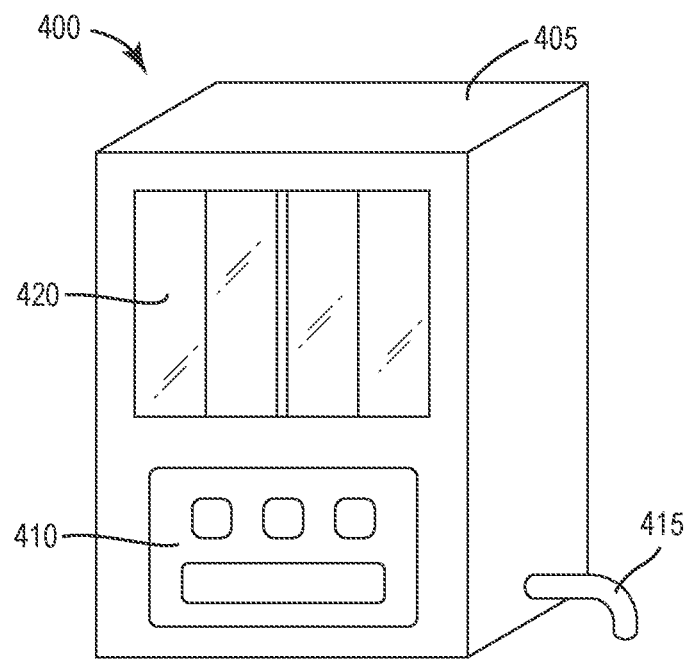
FIG. 4 illustrates a smart mixer with a bottom edge dispenser in accordance with an illustrative embodiment.

FIG. 4 illustrates a smart mixer 400 with a bottom edge dispenser in accordance with an illustrative embodiment. In alternative embodiments, fewer, additional, and/or different components may be included in the mixer. The smart mixer 400 may include a computing device such as the mixer computing device 300 described above with respect to FIG. 3. The smart mixer 400 includes a housing 405. A user interface 410 of the smart mixer 400 may function similarly to the interfaces 125, 205, 310, and 360 as disclosed herein.

The smart mixer also includes an ingredient cartridge compartment 420 that may be similar to the ingredient cartridge compartment 115 of the smart mixer 100 in FIG. 1, in that it can store different removable and replaceable ingredient cartridges for creating recipes in a mixing chamber of the smart mixer 400. The smart mixer 400 also includes a dispenser 415. The dispenser 415 of the smart mixer 400 is a spigot type dispenser that allows a mixture to flow out of it from the smart mixer 400. The dispenser 400 may be controlled by a valve that is controlled by the smart mixer's computing device, a different computing device, or is manually controlled by a user. The valve may also be controlled to be open for a long period of time to allow a liquid mixture that takes a long time to prepare to slowly drip out. The dispenser 415 may also be valuable in dispensing a mixture using gravity. For example, liquids, solutions, powders, solids, etc. may be stored and/or mixed in a chamber or hopper that is generally located above the dispenser 415 in the smart mixer 400. In this way, when a mixture is dispensed, gravity may be used to dispense the mixture without the use of power to pump, scoop, or otherwise transport and dispense the mixture, which can require the use of extra energy from a power source of the smart mixer 400.

Figure 5:
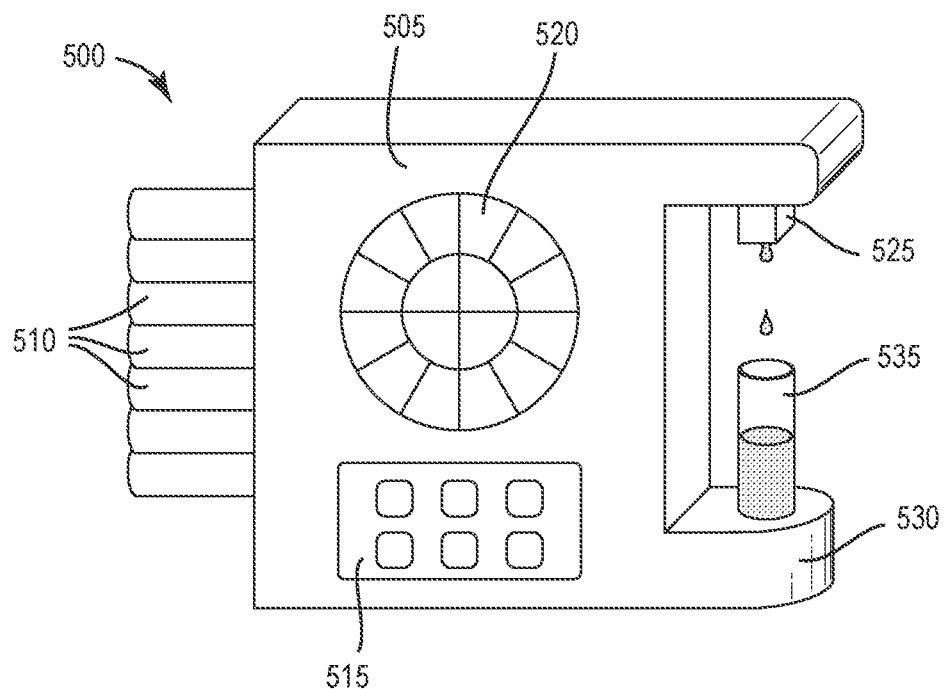
FIG. 5 illustrates a smart mixer with a side cartridge loading and side dispenser in accordance with an illustrative embodiment.

FIG. 5 illustrates a smart mixer 500 with a side cartridge loading and side dispenser in accordance with an illustrative embodiment. In alternative embodiments, fewer, additional, and/or different components may be included in the mixer. The smart mixer 500 may include a computing device such as the mixer computing device 300 described above with respect to FIG. 3. The smart mixer 500 includes a housing 505. The housing 505 is configured to receive ingredient containers 510 that are removable and replaceable as disclosed herein. Here, unlike in FIGS. 1 and 4, the ingredient containers are not located within the housing 505 of the smart mixer 500. The smart mixer 500 also includes a user interface 515. The user interface 515 of the smart mixer 500 may function similarly to the interfaces 125, 205, 310, 360, and 410 as disclosed herein.

The smart mixer 500 also includes an additional user interface 520. The user interface 520 can be used to display additional or similar functions to those accessible through the other user interfaces disclosed herein. In the smart mixer 500, the user interface 520 is designed to be buttons that are directed to specialized functions. For example, the user interface 520 includes an inner circle of buttons and an outer circle of buttons. The inner circle of buttons may be related to a specific specialized function, for example, to display and select certain scents such as promoted or favorite scents that may be added to a mixture. The outer circle of buttons may be related to a single second specialized function, such as favorite or promoted color additives for a mixture (e.g., in a color wheel format). In this way the dual groups of specialized buttons of the user interface 520 can provide specific functions that are used with the smart mixer 500 to prevent a user from having to search or scroll through many menu options on the user interface 515. Other specialized functions might include groupings of specific ingredient types (e.g., spices, related scents), groupings of available temperature settings for a mixture, intensity settings (e.g., what concentration of a mixture should a certain ingredient (s) be), timer settings for when/how long to dispense a mixture, preset or predefined recipes (e.g., celebrity, promoted, favorited, or saved recipes), and any other grouping of specialized functions. Although the smart mixer 500 and the user interface 520 demonstrate a circular pattern and two possible groupings of specialized function buttons, other patterns and number of specialized function groupings may be utilized. In addition, the system may display on the user interface 520 sequential specialized function. For example, if a user selects a first attribute of a mixture, the specialized function buttons of the user interface 520 may change in response to the first selection and provide additional specialized function options that are related to or in addition to the first selection. For example, in a drink mixer, a soft drink may be selected in a first selection. The user interface 520 may then provide related selection options, such as options for how much carbonation the user would like in their soft drink.

The smart mixer 500 also includes a stand 530 for a container 535 in which a mixture may be input by a dispenser 525.

Figures 6, 7:
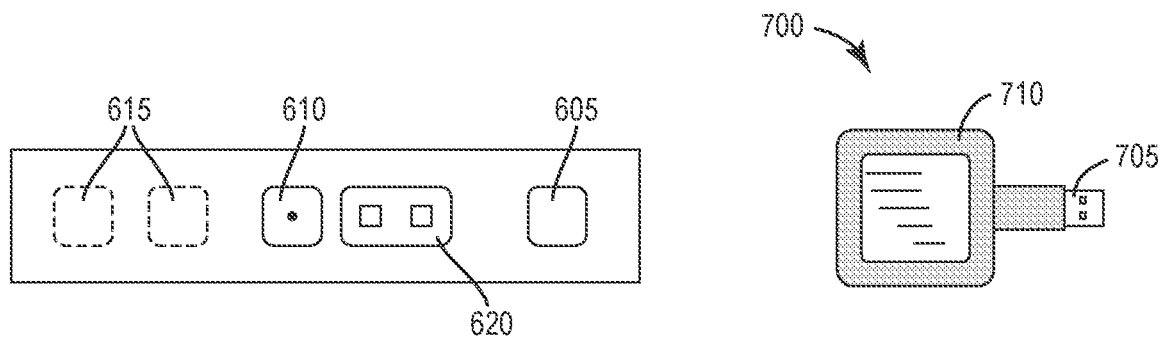
FIG. 6 illustrates a wearable smart mixer and/or sensor in accordance with an illustrative embodiment.
FIG. 7 illustrates a scanner device for use with a smart mixer in accordance with an illustrative embodiment.

FIG. 6 illustrates a wearable 600 smart mixer and/or sensor in accordance with an illustrative embodiment. In alternative embodiments, fewer, additional, and/or different components may be included. The wearable 600 is a wrist or arm band. However, other wearables are contemplated. The wearable 600 includes ingredient cartridges 615, a dispenser 610, a user interface 620, and a sensor 605. The ingredient cartridges 615, the dispenser 610, and the user interface 620 can function similarly to the aspects of the smart mixer devices described above in FIGS. 1 and 3-5. The sensor 605 can be used to take certain measurements that can be sent to other computing devices and be used to adjust or create recipes based on the conditions sensed. For example, a sensor may sense a rise in temperature at the skin of a user wearing the wearable 600. A smart mixer (either the wearable itself or another smart mixer that the wearable 600 can communicate with) can then make a drink that is configured to hydrate the user based on an assumption based on the rise in skin surface temperature that the user is exercising and/or perspiring. Such sensors may be incorporated into other devices that can sense conditions not only related to a user, but also to an environment such as the air in a room, noise, pressure, odors, light levels, biometric measurements (e.g., heart rate, of liquids like urine/sweat/saliva), other chemical measurements and any other condition that may be used to adjust or create a recipe.

FIG. 7 illustrates a scanner device 700 for use with a smart mixer in accordance with an illustrative embodiment. In alternative embodiments, fewer, additional, and/or different components may be included. The scanner device 700 includes a universal serial bus (USB) port 705 that can be used to connect the scanner device to computing devices such as smart mixers or other computing devices. Other methods of connecting to a computing device or smart mixer are also contemplated. The scanner device 700 can be used to optically scan something so that the scanner device 700 and/or a computing device can process image data to create or adjust a recipe. For example, a user may scan a clothing item, and a smart mixer may determine a color of the clothing to create a lipstick with a matching color. In another example, a fabric with a stain may be scanned so that a smart mixer can determine a fabric type and/or a stain type on the fabric. With this information, the smart mixer can make a custom detergent to treat the stain and clean the fabric.

Figure 8:
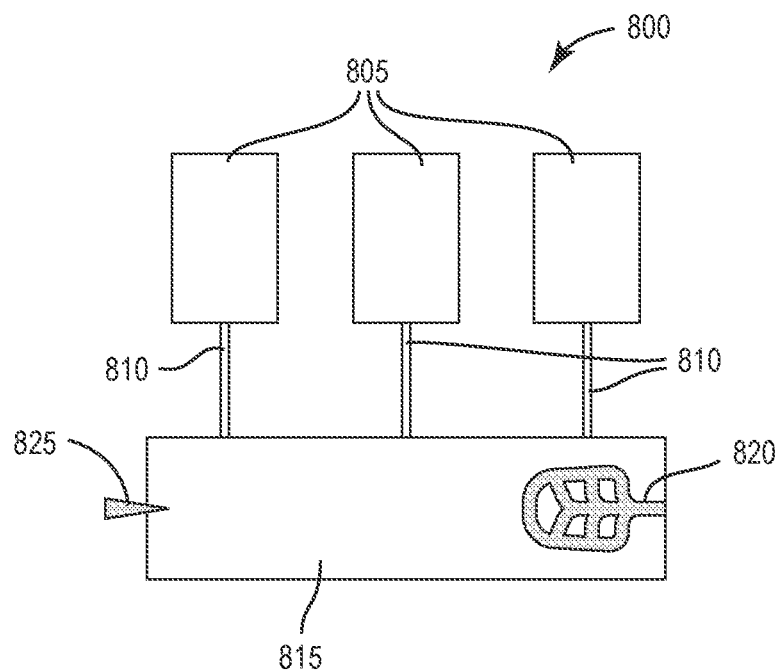
FIG. 8 illustrates ingredients and a mixing chamber in accordance with an illustrative embodiment.

FIG. 8 illustrates ingredients 805 and a mixing chamber 815 in accordance with an illustrative embodiment. In alternative embodiments, fewer, additional, and/or different components may be included. The ingredients 805 can be inserted into the mixing chamber 815 through tubes 810. The ingredients can be mixed by a mixer or impeller 820. The mixture can then be output by a dispenser 825. Where a motor is used, such as the mixer or impeller 820, the system may capture energy when the motor is braked or stopped, for example using mag-lev technology. In various embodiments, a mixture may be mixed in a variety of ways. For example, a mixing and/or dispensing chamber may be a membrane that can change shape in response to actuators that impact it, temperature, pressure (e.g., air pressure outside the membrane), or other forces. In such an embodiment, the membrane may be caused to change shape to dispense or mix the ingredients therein. Such an embodiment may be advantageous in a smart mixer where there is more than one mixing and/or dispensing chambers. As a mixture is passed out of a first membrane chamber, that first chamber can collapse as a second chamber that the mixture passes into expands. Thus, a housing of a smart mixture can advantageously be smaller with multiple membrane chambers than it would be with multiple fixed volume chambers. Using chambers such as membrane chambers that can change volume, a smart mixer can also change the pressure inside a chamber by changing volume. In various embodiments, a chamber may also change its pressure and/or volume by introducing additional ingredients (e.g., liquid, air, etc.) into the chamber.

Figure 9:
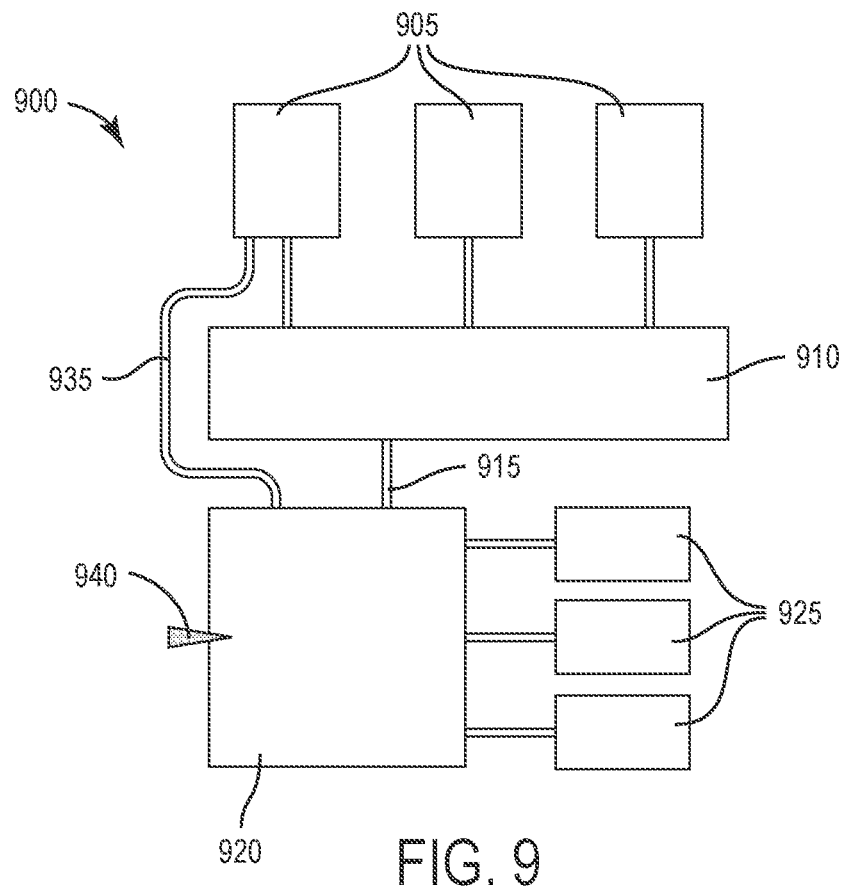
FIG. 9 illustrates multi-stage mixing chambers in accordance with an illustrative embodiment.

FIG. 9 illustrates multi-stage mixing chambers 910 and 915 in accordance with an illustrative embodiment. In alternative embodiments, fewer, additional, and/or different components may be included. A first set of ingredients 905 can be inserted into the mixing chamber 910 according to a recipe. The mixture can then be inserted into a mixing chamber 920 through a tube 915, where additional ingredients 925 can be added to the mixture. One of the first set of ingredients may also be added to the mixture in the second mixing chamber 920 through a tube 935. The mixture can then be output through a dispenser 940

Figure 10:
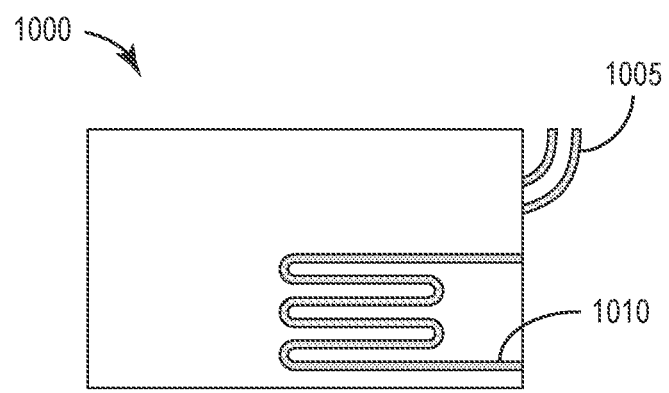
FIG. 10 illustrates a mixing chamber with a heating element in accordance with an illustrative embodiment.

FIG. 10 illustrates a mixing chamber 1000 with a heating element 1010 in accordance with an illustrative embodiment. In alternative embodiments, fewer, additional, and/or different components may be included. The mixing chamber 1000 also shows ingredient input tubes 1005 that may be used to insert ingredients to be heated in the mixing chamber 1000.

Figure 11:
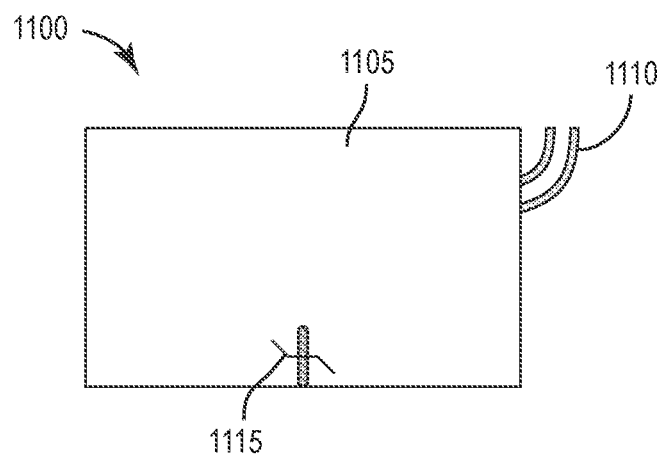
FIG. 11 illustrates a mixing chamber with a blending blade in accordance with an illustrative embodiment.

FIG. 11 illustrates a mixing chamber 1100 with a blending blade 1115 in accordance with an illustrative embodiment. In alternative embodiments, fewer, additional, and/or different components may be included. The mixing chamber 1000 also shows ingredient input tubes 1110 that may be used to insert ingredients to be blended in the mixing chamber 1100.

Figure 12:
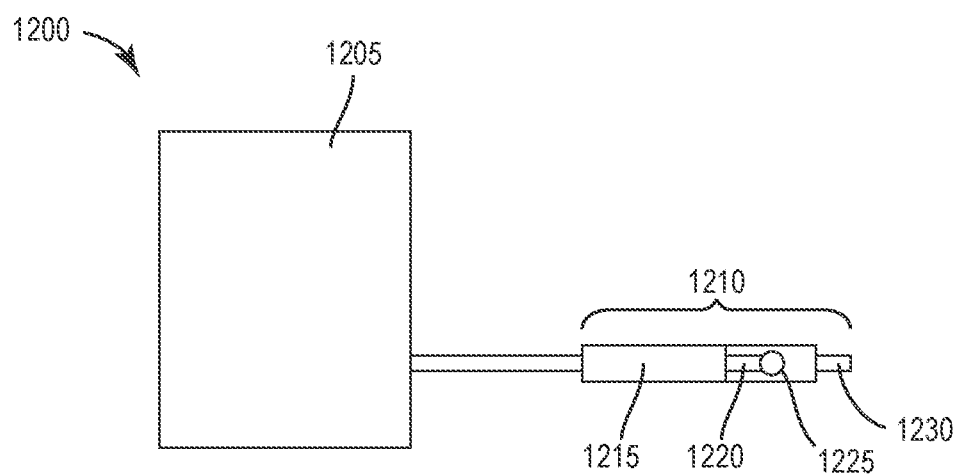
FIG. 12 illustrates a mixing chamber connected to a vaporizer device in accordance with an illustrative embodiment.

FIG. 12 illustrates a mixing chamber 1205 connected to a vaporizer device 1210 in accordance with an illustrative embodiment. In alternative embodiments, fewer, additional, and/or different components may be included. The vaporizer device 1210 in this embodiment is a dispenser for a smart mixer 1200 with the mixing chamber 1205. The vaporizer 1210 includes a dispensing chamber 1215, wicks 1220, a heating element 1225, and a vaporizer dispensing component 1230. The mixture output from the mixing chamber 1205 is output to the dispensing chamber 1215, where the mixture can be vaporized and output by the vaporizer 1210. The vaporizer 1210 may also be detachable from the smart mixer 1200 in various embodiments so that the mixture can be portable and dispensed wherever the user would like.

Figure 13:
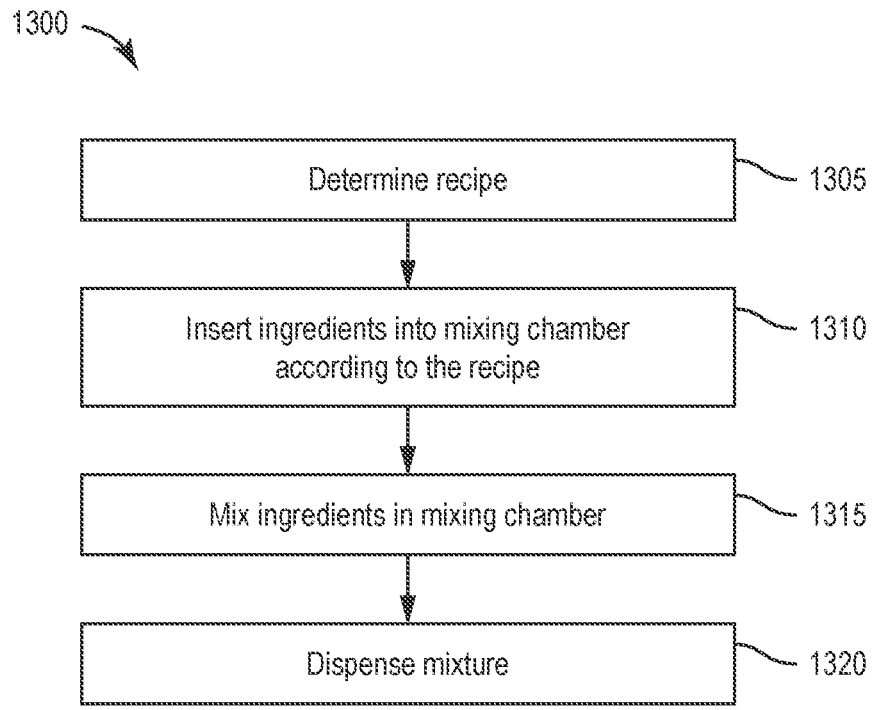
FIG. 13 is a flow diagram illustrating a method of mixing a recipe in accordance with an illustrative embodiment.

FIG. 13 is a flow diagram illustrating a method 1300 of mixing a recipe in accordance with an illustrative embodiment. In alternative embodiments, fewer, additional, and/or different operations may be performed. Also, the use of a flow diagram is not meant to be limiting with respect to the order of operations performed.

Figure 14:
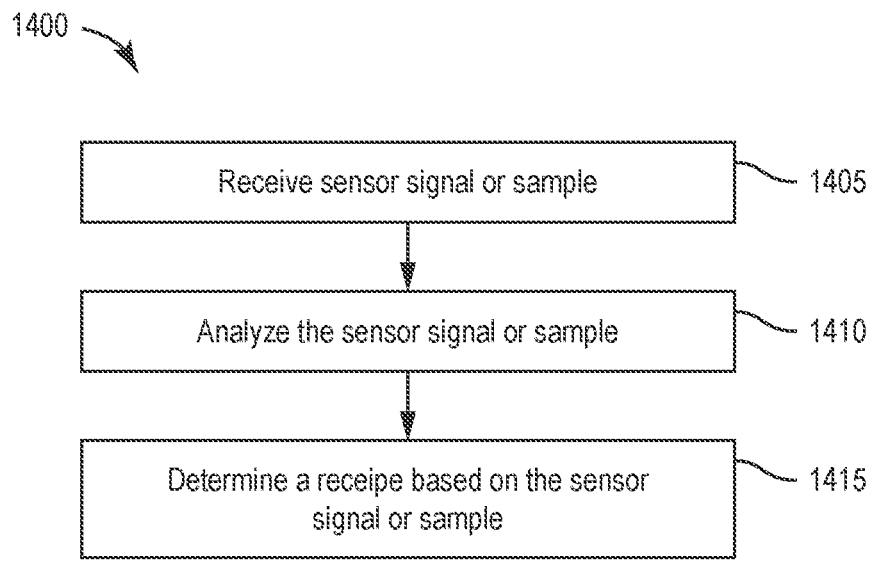
FIG. 14 is a flow diagram illustrating a method of determining a recipe based on a sensor in accordance with an illustrative embodiment.

FIG. 14 is a flow diagram illustrating a method 1400 of determining a recipe based on a sensor in accordance with an illustrative embodiment. In alternative embodiments, fewer, additional, and/or different operations may be performed. Also, the use of a flow diagram is not meant to be limiting with respect to the order of operations performed.

Figure 15:
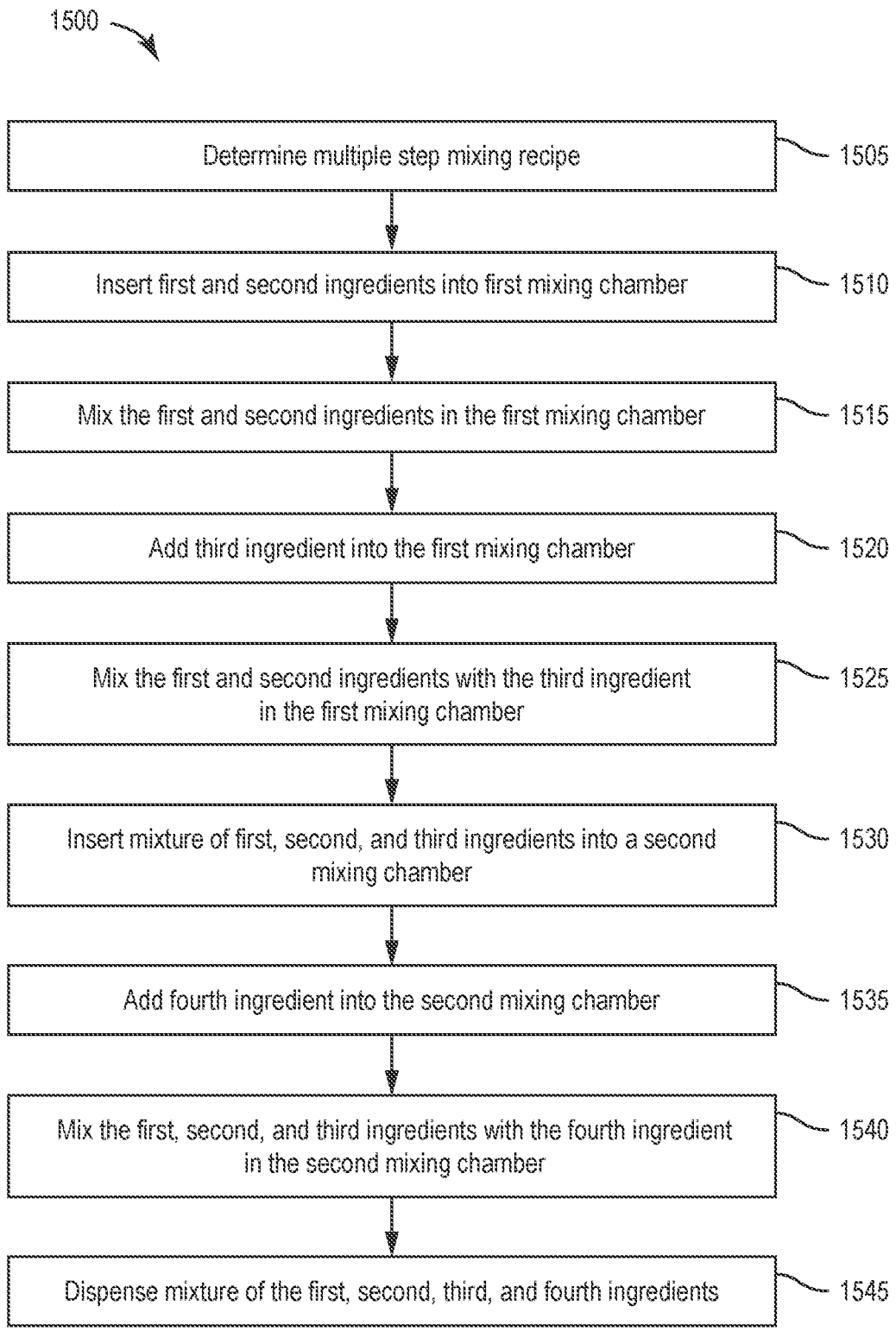
FIG. 15 is a flow diagram illustrating a method for multi-stage mixing of a recipe in accordance with an illustrative embodiment.

FIG. 15 is a flow diagram illustrating a method 1500 for multi-stage mixing of a recipe in accordance with an illustrative embodiment. In alternative embodiments, fewer, additional, and/or different operations may be performed. Also, the use of a flow diagram is not meant to be limiting with respect to the order of operations performed.

Figure 16:
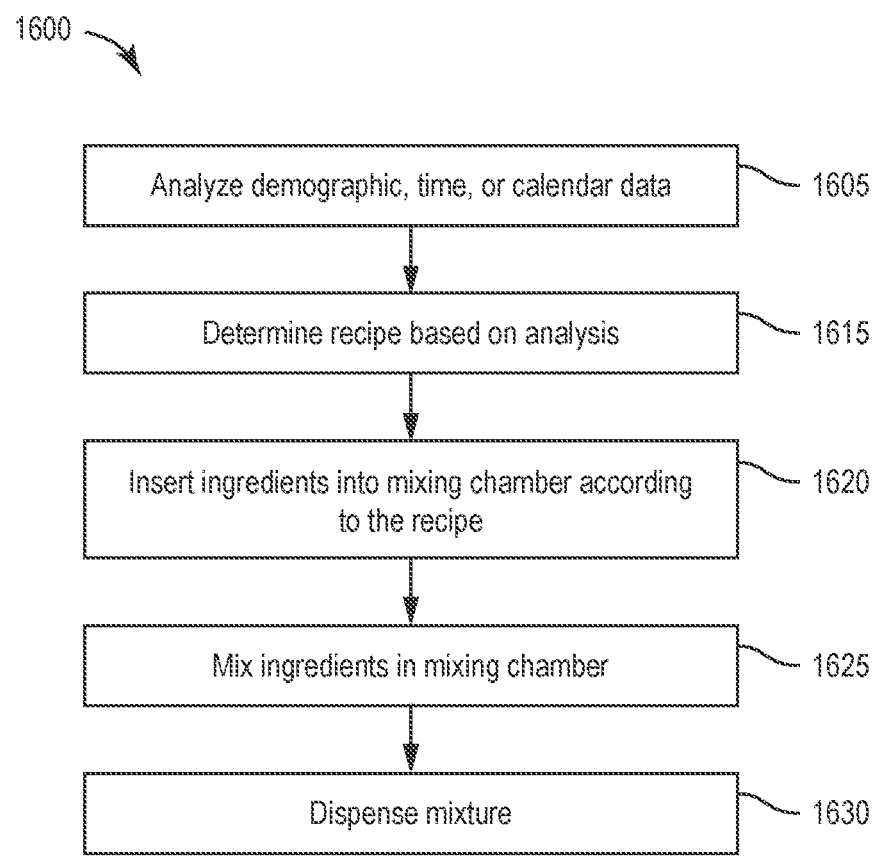
FIG. 16 is a flow diagram illustrating a method for determining a recipe based on demographic, calendar, time, or other data in accordance with an illustrative embodiment.

FIG. 16 is a flow diagram illustrating a method 1600 for determining a recipe based on demographic, calendar, time, or other data in accordance with an illustrative embodiment. In alternative embodiments, fewer, additional, and/or different operations may be performed. Also, the use of a flow diagram is not meant to be limiting with respect to the order of operations performed. For example, a smart mixer integrated into a shirt may mix and/or release a different fragrance in business hours than it would at night. In another example, that smart mixer may mix and/or release a different fragrance depending on a demographic of the wearer, such as whether the wearer is a man or a woman. In another example, a scent may be different based on a calendar appointment or item. For example, a calendar item for a business dinner may mix and/or release a different scent than a scent mixed and/or released for a romantic date.

In an illustrative embodiment, any of the operations described herein can be implemented at least in part as computer-readable instructions stored on a computer-readable medium or memory. Upon execution of the computer-readable instructions by a processor, the computer-readable instructions can cause a computing device to perform the operations.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A device for dispensing a mixture of ingredients, the device comprising:
    a cartridge chamber configured to house a plurality of ingredient cartridges, each ingredient cartridge of the plurality of ingredient cartridges comprises a different ingredient;
    a mixing chamber configured to mix two or more ingredients from the plurality of ingredient cartridges;
    a dispenser for dispensing a mixture that has been mixed by the mixing chamber;
    a processor configured to receive a recipe comprising a plurality of types of ingredients and amounts for each of the types of ingredients; and
    wherein the processor is configured to control the mixing chamber and the plurality of ingredient cartridges to insert amounts of the plurality of types of ingredients into the mixing chamber according to the recipe; and
    wherein the dispenser is configured to output the mixture resulting from mixing amounts of the plurality of types of ingredients by the mixing chamber.

2. The device of claim 1, wherein the device is further configured to dispense the mixture as one of a vapor, a fine powder, a mist, or a liquid.

3. The device of claim 1, further comprising a user interface configured to control via the processor the mixing chamber.

4. The device of claim 1, further comprising a user interface configured to receive input from a user to specify the recipe.

5. The device of claim 1, further comprising a plurality of dispensers comprising the dispenser.

6. The device of claim 5, further comprising a user interface configured to determine which of the plurality of dispensers to dispense the mixture.

7. The device of claim 1, further comprising one or more dispensing chambers configure to receive the mixture from the mixing chamber and to provide the mixture to the dispenser.

8. The device of claim 7, further comprising a user interface configure to determine which of the one or more dispending chambers to receive the mixture from the mixing chamber.

9. The device of claim 1, further comprising a user interface configured to download the recipe via a network to the device.

10. The device of claim 1, further comprising a vaporizing device configured to receive the mixture output from the mixing chamber and vaporize the mixture for output via the dispenser.

11. A system for dispensing a mixture of ingredients, the device comprising:
    a smart mixer comprising:
        a cartridge chamber configured to house a plurality of ingredient cartridges, each ingredient cartridge of the plurality of ingredient cartridges comprises a different ingredient;
        a mixing chamber configured to mix two or more ingredients from the plurality of ingredient cartridges;
        a dispenser for dispensing a mixture that has been mixed by the mixing chamber; and a processor configured to control the mixing chamber and the plurality of ingredient cartridges; and a computing device in communication with the smart mixer via one or more networks and comprising a user interface configured to one of manage or control the smart mixer; and wherein the processor of the smart mixer is configured to receive information on a recipe from the computing device and to control the mixing chamber and the plurality of ingredient cartridges to insert amounts of the plurality of types of ingredients into the mixing chamber according to the recipe.

12. The system of claim 11, wherein the dispenser is further configured to dispense the mixture as one of a vapor, a fine powder, a mist, or a liquid.

13. The system of claim 11, wherein the user interface is further configured to control via the processor the mixing chamber.

14. The system of claim 11, wherein the user interface is further configured to receive input from a user to specify the recipe.

15. The system of claim 11, wherein the user interface is further configured to download the recipe to the smart mixer.

16. A device for dispensing a mixture of ingredients, the device comprising:

a cartridge chamber configured to house a plurality of ingredient cartridges, each ingredient cartridge of the plurality of ingredient cartridges comprises a different ingredient;

a mixing chamber configured to mix two or more ingredients from the plurality of ingredient cartridges;

a dispenser for dispensing a mixture that has been mixed by the mixing chamber;

a processor is configured to control the mixing chamber and the plurality of ingredient cartridges; and a user interface configured to received input from a user to one of control or manage the device; and wherein the processor is configured to receive information on a recipe from the user interface and to control the mixing chamber and the plurality of ingredient cartridges to insert amounts of the plurality of types of ingredients into the mixing chamber according to the recipe.

17. The device of claim 16, wherein the device is further configured to dispense the mixture as one of a vapor, a fine powder, a mist, or a liquid.

18. The device of claim 16, wherein the user interface is further configured to control via the processor the mixing chamber.

19. The device of claim 16, wherein the user interface is further configured to receive input from a user to specify the recipe.

20. The device of claim 16, wherein the user interface is further configured to download the recipe to the processor.

* * * * *